US 6,254,784 B1
Jul. 3, 2001

United States Patent
Nayak et al.

(54) OPTICAL INTERFACE DETECTION SYSTEM FOR CENTRIFUGAL BLOOD PROCESSING

(75) Inventors: Abinash Nayak, Grayslake; Clint D. Luckinbill, Carpentersville; John T. Foley, Wheeling; Minh D. Tran, Grayslake; James R. Bradley, Palatine; Timothy J. Patno, Mundelein, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/961,340

(22) Filed: Oct. 30, 1997

(51) Int. Cl.$^7$ .............................. B01D 17/12; G01N 33/48
(52) U.S. Cl. .................... 210/745; 210/94; 210/512.1; 210/787; 356/39; 494/10; 494/37; 604/4.01; 702/71; 702/73
(58) Field of Search .................... 210/85, 94, 360.1, 210/380.1, 512.1, 739, 745, 782, 787, 789; 494/1, 10, 37; 604/5, 4.01, 5.01; 356/39, 40; 702/31, 32, 66, 71, 73, 75

(56) References Cited

U.S. PATENT DOCUMENTS

| | | | |
|---|---|---|---|
| 3,727,066 | 4/1973 | Louderback et al. | 356/436 |
| 3,752,995 | 8/1973 | Leidholz | 356/436 |
| 3,778,171 | 12/1973 | Chervenka | 494/10 |
| 4,409,820 | 10/1983 | Nash | 494/110 |
| 4,468,219 | 8/1984 | George et al. | 604/66 |
| 4,557,719 | 12/1985 | Neumann et al. | 494/37 |
| 4,604,086 | 8/1986 | Benko et al. | 494/10 |
| 4,810,090 | 3/1989 | Boucher et al. | 356/39 |
| 5,104,526 | 4/1992 | Brown et al. | 210/94 |
| 5,316,666 | 5/1994 | Brown et al. | 210/94 |
| 5,316,667 | 5/1994 | Brown et al. | 210/85 |
| 5,400,261 * | 3/1995 | Reynolds | 702/73 |
| 5,437,598 | 8/1995 | Antwiler | 494/1 |
| 5,573,678 | 11/1996 | Brown et al. | 210/782 |
| 5,592,402 * | 1/1997 | Beebe et al. | 702/66 |
| 5,605,842 | 2/1997 | Langley et al. | 436/177 |
| 5,611,997 | 3/1997 | Langley et al. | 422/73 |
| 5,628,915 | 5/1997 | Brown et al. | 210/782 |
| 5,639,382 | 6/1997 | Brown | 210/739 |
| 5,656,163 * | 8/1997 | Brown | 210/94 |
| 5,948,271 * | 9/1999 | Wardwell et al. | 210/94 |
| 5,958,250 * | 9/1999 | Brown et al. | 210/94 |
| 5,961,842 * | 10/1999 | Min et al. | 210/745 |
| 5,980,757 * | 11/1999 | Brown et al. | 494/10 |
| 5,980,760 * | 11/1999 | Min et al. | 210/745 |
| 6,063,292 * | 5/2000 | Leung | 210/739 |

OTHER PUBLICATIONS

Liles et al, A comparative trial of granulocyte–stimulating factor and dexamethasone, separately and in combination for the mobilization of neutrophils in the peripheral blood of normal volunteers, Transfusion, vol. 37, Mar. 1997.

Dumont et al., Enhanced Flow Cytometric Method for Counting Very Low Numbers of White Cells in Platelet Products, Cytometry, 26:311–318 (1996).

* cited by examiner

Primary Examiner—Joseph W. Drodge
(74) Attorney, Agent, or Firm—Daniel D. Ryan; Bradford R. L. Price; Michael C. Mayo

(57) ABSTRACT

A centrifuge for continuously separating the various constituents of blood or other biological fluids includes a rotating bowl having high-G and low-G walls. An inwardly directed ramped surface on the high-G wall interacts with an interface region between the separated fluid constituents to provide an optically detectable indication of the position of the interface between the high-G and low-G walls. An optical sensor sensing each passage of the ramped surface past a point develops a changing signal indicative of the interface position. Signal processing circuitry responsive to the signal measures such signal parameters as peak amplitude, signal area and signal shape. By so monitoring these signal parameters, a better indication of actual interface position between the high-G and low-G walls can be obtained. This, in turn, results in better control over centrifuge operation and improved separation of the desired fluid components.

49 Claims, 10 Drawing Sheets

OPTICAL INTERFACE DETECTION SYSTEM FOR CENTRIFUGAL BLOOD PROCESSING

FIELD OF THE INVENTION

This invention relates generally to centrifugal processing systems and apparatus.

BACKGROUND OF THE INVENTION

Various blood processing systems now make it possible to collect particular blood constituents, rather than whole blood, from donors. Typically, in such systems, whole blood is drawn from a donor, the particular blood component or constituent is removed and collected, and the remaining blood constituents are returned to the donor. By thus removing only particular constituents, less time is needed for the donor's body to return to normal, and donations can be made at more frequent intervals than when whole blood is collected. This increases the overall supply of blood constituents, such as plasma and platelets, made available for health care.

Whole blood is typically separated into its constituents through centrifugation. This requires that the whole blood be passed through a centrifuge after it is withdrawn from, and before it is returned to, the donor. To avoid contamination and possible infection of the donor, the blood is preferably contained within a sealed, sterile system during the entire centrifugation process. Typical blood processing systems thus include a permanent, reusable centrifuge assembly containing the hardware that spins and pumps the blood, and a disposable, sealed and sterile fluid processing assembly that actually makes contact with the donor's blood. The centrifuge assembly engages and spins the fluid processing assembly during a collection procedure. The blood, however, makes actual contact only with the fluid processing assembly, which is used only once and then discarded.

As the whole blood is spun by the centrifuge, the heavier components, such as red blood cells, move outwardly away from the center of rotation toward the outer or "high g" wall of a separating chamber included as part of the fluid processing assembly. The lighter components, such as platelet-rich plasma, migrate toward the inner or "low g" wall of the separating chamber. Typically, an intermediate layer of white blood cells forms an interface between the platelet-rich plasma and red blood cell components of the whole blood during centrifugation. Various ones of these components can be selectively removed from the whole blood by forming appropriately located channeling seals and outlet ports in the separating chamber of the fluid processing assembly. Proper separation requires, however, that the interface between the platelet-rich plasma and the red blood cells be located within a particular zone between the high g and low g walls of the separating chamber. Displacement of the interface from the desired location can result in low platelet yield if the interface is too near the high g wall, or can result in a high whole blood cell count in the extracted plasma if the interface is located too near the low g wall. Good platelet yields along with low whole blood cell counts are achieved when the interface is maintained at the proper, desired location.

Various known centrifuges, such as those shown and described in U.S. Pat. No. 5,316,667, are operable to automatically keep the interface within the desired zone as the centrifuge operates. Typically, the separating chamber of the fluid processing assembly is loaded between the bowl and spool of a centrifuge. A ramped surface formed on the interior outer wall of the bowl deflects the high g wall of the separating chamber inwardly relative to the axis of rotation. The interface between the generally dark, opaque whole blood cell layer and the generally light, clear plasma layer appears as a line projected onto the ramped surface. Where, exactly, the line appears on the ramped surface is a function of the position of the interface between the high g and low g walls of the separating chamber. Accordingly, the position of the line on the ramped surface can be used to gauge the position of the interface between the high g and low g surfaces.

Automatic control over the location of the interface is achieved by sensing the position of the line on the ramped surface and thereafter adjusting the centrifuge operating parameters to place and keep the line within desired limits. In particular, by controlling the rate at which platelet-rich plasma is withdrawn from the separating chamber, the line can be "moved" up or down on the ramped surface. Typically, an optical sensor is used to sense the position of the line on the ramped surface. As the centrifuge spins past the sensor, the sensor develops an electrical pulse having a width related to the position of the line on the ramped surface. As the line moves closer to the high g wall of the separating chamber, the pulse width increases. As the line moves closer to the low g wall, the pulse width narrows. By sensing the width of the pulses developed by the optical sensor and thereafter using the pulse width to increase or decrease the rate at which platelet-rich plasma is withdrawn from the separating chamber, the line can be kept within desired positional limits on the ramped surface.

Prior, optically based interface detection and control systems responded only to the width of the pulse developed by the optical sensor and assumed that pulse width alone was a reliable indicator of the position of the interface line on the ramped surface. However, experience has shown that a variety of abnormalities or unusual operating conditions can arise that make pulse width, by itself, an unreliable sole indicator of proper interface positioning. For example, unusually high or low platelet counts in the donor's blood can change the light transmisitivity of the plasma and thus the apparent width of the detected pulses with no real change in the actual position of the interface line on the ramped surface. Similarly, a temporary accumulation of platelets on the ramped surface can cause a change in pulse width with no real change in the interface line position. Nevertheless, prior systems, which responded only to the width of the pulses developed by the optical sensor, would view either occurrence as requiring corrective action. The result would be to shift the interface away from the optimum position.

SUMMARY OF THE INVENTION

The invention provides a centrifugal processing system comprising a centrifuge having a rotatable bowl assembly including a high g wall and a ramped surface formed in the high g wall. The centrifugal processing system further comprises a fluid processing assembly including a separating chamber receivable in the bowl assembly and engaging the high g wall. The centrifugal processing system further comprises an optical detector operative to sense the position of an interface between two dissimilar components of a fluid within the separating chamber during centrifugation and to develop a signal indicative of the position of the interface relative to the ramped surface. A signal processor responsive to the wave shape and amplitude of the signal developed by the optical sensor and operable to develop control outputs based on the shape and amplitude of the signal is also included. The centrifugal processing system further includes control circuitry coupled to the centrifuge and responsive to the control outputs for controlling the operation of the centrifuge in accordance with the sensed shape and amplitude of the signal developed by the optical sensor so as to maintain the position of the interface within a desired zone relative to the ramped surface.

The invention also provides an interface position control system for controlling the position of an interface between the component layers of a fluid during centrifugation. The system includes an energy source operable to direct energy onto the interface. The energy thus directed is substantially absorbed by one of the component layers and is substantially reflected by the other of the component layers. A sensor operable to sense the energy reflected by the reflective one of the component layers and to develop a signal indicative of the intensity of the energy thus reflected is also provided. The system further includes a signal processor operable to sense the magnitude, duration and wave-shape of the signal developed by the sensor.

A comparator is coupled to the signal processor and is operable to compare the wave-shape of the signal to preselected known wave-shapes. A control system responsive to the signal and to the comparator is provided and is operable to control the operating parameters of the centrifugation process in accordance with the sensed magnitude, duration and wave-shape of the signal sensed by the sensor.

The invention also provides a method of operating a centrifuge of the type having a ramped surface and an optical detector for developing a signal indicative of the position of a constituent interface relative to a ramped surface carried within the centrifuge. The method includes the steps of sensing predetermined parameters of the signal, comparing the sensed parameters against predetermined standards, and varying operating parameters of the centrifuge in accordance with the sensed predetermined parameters of the signal.

The invention also provides an improvement in a centrifuge of the type having a ramped surface and an optical detector for developing a signal indicative of the position of a constituent interface relative to a ramped surface carried within the centrifuge. The improvement includes a sensor for sensing predetermined parameters of the signal, a comparator for comparing the sensed parameters against predetermined standards, and a controller for varying operating parameters of the centrifuge in accordance with the sensed predetermined parameters of the signal.

It is an object of the present invention to provide a new and improved interface detection and control system for detecting and controlling the position of an interface between dissimilar materials in a centrifuging process.

It is a further object of the invention to provide an interface detection and control system that automatically responds to changing or abnormal conditions to keep an interface between dissimilar materials properly located during a centrifuging process.

It is a further object of the invention to provide an interface detection and control system that is flexible and that can be readily adapted to operate under varying or diverse operating conditions.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, wherein like reference numerals identify like elements, and wherein:

DESCRIPTION OF THE PREFERRED EMBODIMENTS

Figure 1:
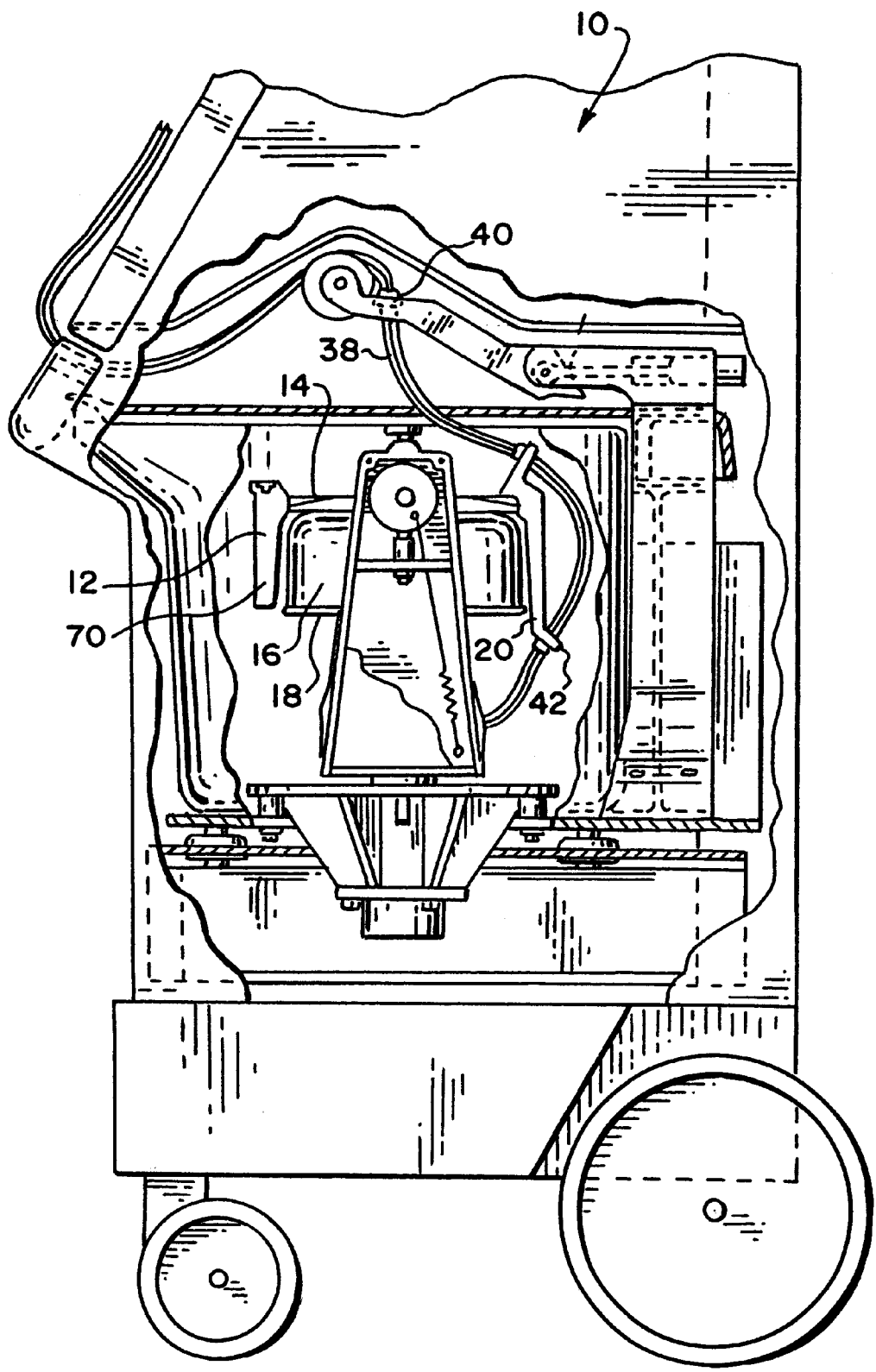
FIG. 1 is a side elevation view, with portions broken away and in section, of a blood processing system comprising a centrifuge with an interface detection system, which embodies features of the invention, the bowl and spool of the centrifuge being shown in their operating position.
Figure 2:
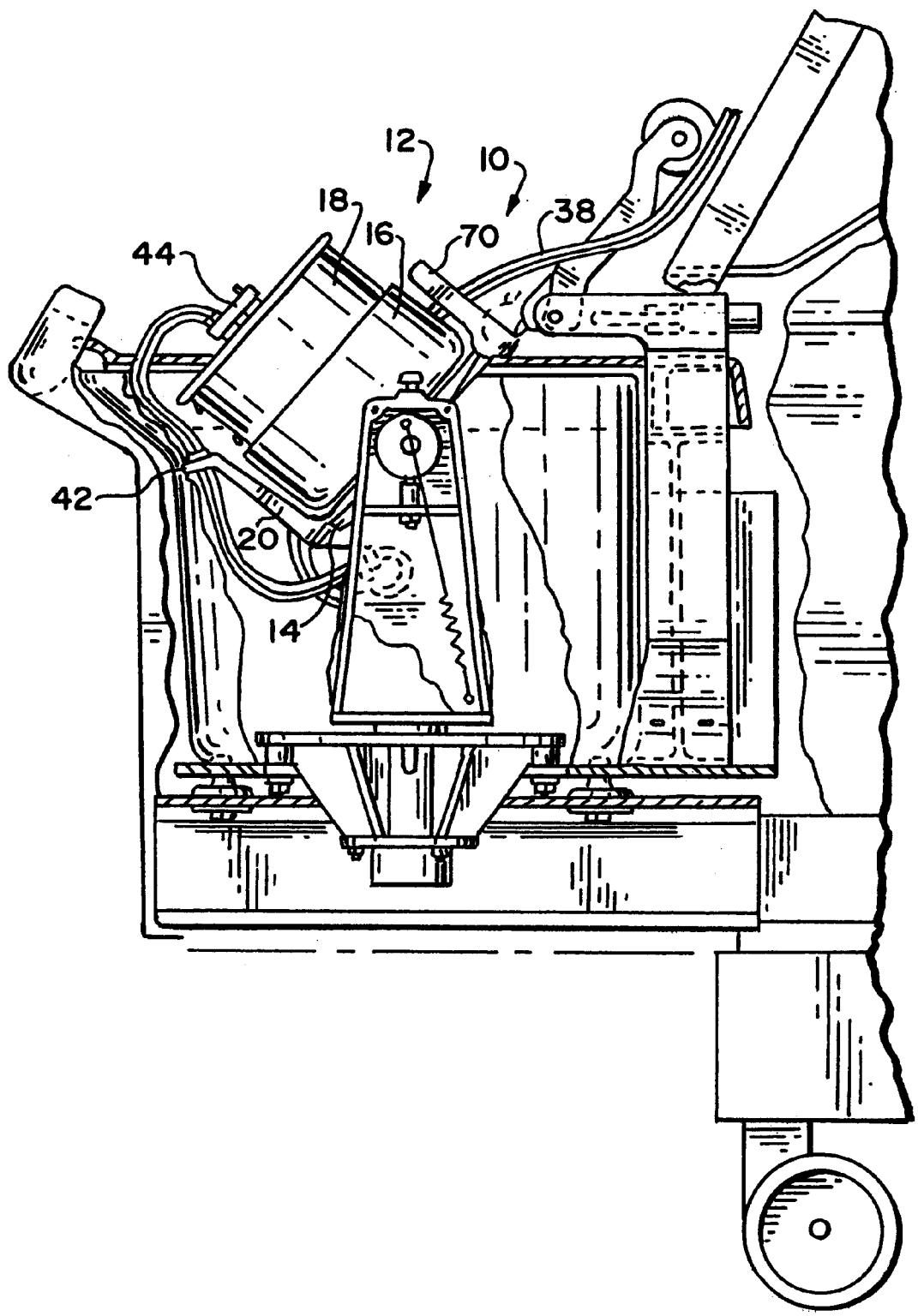
FIG. 2 is a side elevation view, with portions broken away and in section, of the centrifuge shown in FIG. 1, with the bowl and spool of the centrifuge shown in their upright position for receiving a blood processing chamber.

FIGS. 1 and 2 show a blood processing system 10, which incorporates an interface controller 12 that embodies features of the invention. The invention is described in the context of blood processing, because it is well suited for use in this environment. Still, it should be appreciated that use of the invention is not limited to blood processing. The features of the invention can be used in association with any system in which materials that can be optically differentiated are handled.

A. The Centrifuge

The system 10 includes a centrifuge 14 used to centrifugally separate blood components. In the illustrated embodiment, the centrifuge 14 separates whole blood to harvest red blood cells (RBC), platelet concentrate (PC), and platelet-poor plasma (PPP). The centrifuge 14 can also be used to harvest mononuclear cells and granulocytes from blood.

The centrifuge 14 is of the type shown in U.S. Pat. No. 5,316,667, which is incorporated herein by reference. The centrifuge comprises a bowl 16 and a spool 18. The bowl 16 and spool 18 are pivoted on a yoke 20 between an upright position, as FIG. 2 shows, and a suspended position, as FIG. 1 shows.

When upright, the spool 18 can be opened by movement at least partially out of the bowl 16, as FIG. 2 shows. In this position, the operator wraps a flexible blood processing chamber 22 (see FIG. 3) about the spool 18. Closure of the spool 18 and bowl 16 encloses the chamber 22 for processing. When closed, the spool 18 and bowl 16 are pivoted into the suspended position for rotation about an axis.

B. The Blood Processing Chamber

Figure 4:
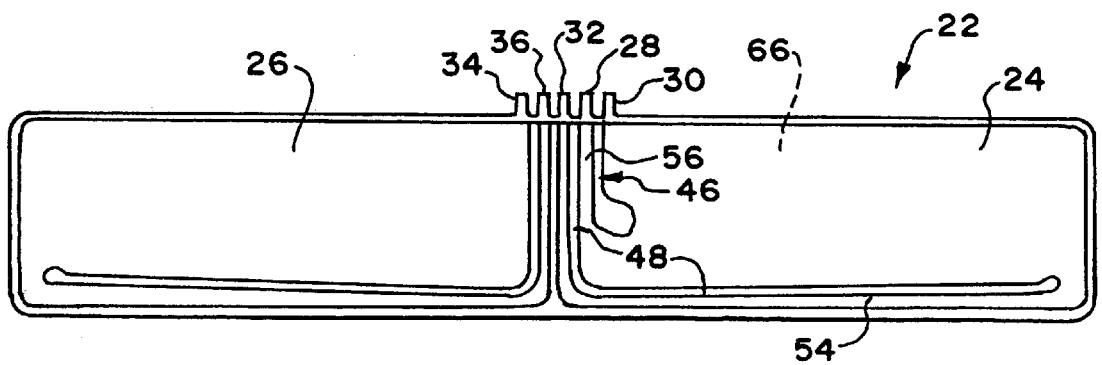
FIG. 4 is a plan view of the blood processing chamber shown in FIG. 3, out of association with the spool.

The blood processing chamber 22 can be variously constructed. FIG. 4 shows a representative preferred embodiment. The chamber 22 shown in FIG. 4 provides multi-stage processing. A first stage 24 separates WB into RBC and platelet-rich plasma (PRP). A second stage 26 separates the PRP into PC and PPP.

Figure 3:
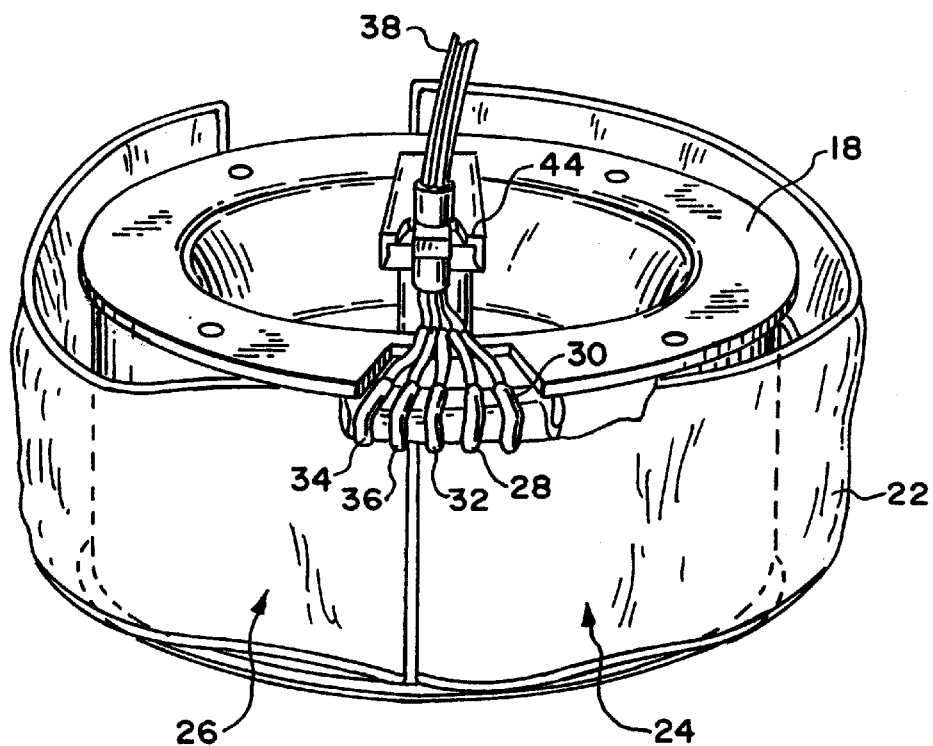
FIG. 3 is a top perspective view of the spool of the centrifuge shown in FIG. 2, in its upright position and carrying the blood processing chamber.

As FIGS. 3 and 4 best show, a port 28 conveys WB into the first stage 24. Ports 30 and 32, respectively, convey PRP and RBC from the first stage 24. RBC is returned to the donor. A port 34 conveys PRP into the second stage 26. A port 36 conveys PPP from the second stage 26, leaving PC in the second stage 26 for resuspension and transfer to one or more storage containers. The ports 28, 30, 32, 34, and 36 are arranged side-by-side along the top transverse edge of the chamber 22.

As FIGS. 1 and 3 best show, a tubing umbilicus 38 is attached to the ports 28, 30, 32, 34, and 36. The umbilicus 38 interconnects the first and second stages 24 and 26 with each other and with pumps and other stationary components located outside the rotating components of the centrifuge 14 (not shown). As FIG. 1 shows, a non-rotating (zero omega) holder 40 holds the upper portion of the umbilicus 38 in a non-rotating position above the suspended spool 18 and bowl 16. A holder 42 on the yoke 20 rotates the mid-portion of the umbilicus 38 at a first (one omega) speed about the suspended spool 18 and bowl 16. Another holder 44 (see FIG. 2) rotates the lower end of the umbilicus 38 at a second speed twice the one omega speed (the two omega speed), at which the suspended spool 18 and bowl 16 also rotate. This known relative rotation of the umbilicus 38 keeps it untwisted, in this way avoiding the need for rotating seals.

As FIG. 4 shows, a first interior seal 46 is located between the PRP collection port 30 and the WB inlet port 28. A second interior seal 48 is located between the WB inlet port 28 and the RBC collection port 32. The interior seals 46 and 48 form a WB inlet passage 50 and a PRP collection region 52 in the first stage 24. The second seal 48 also forms a RBC collection passage 54 in the first stage 24.

Figure 5:
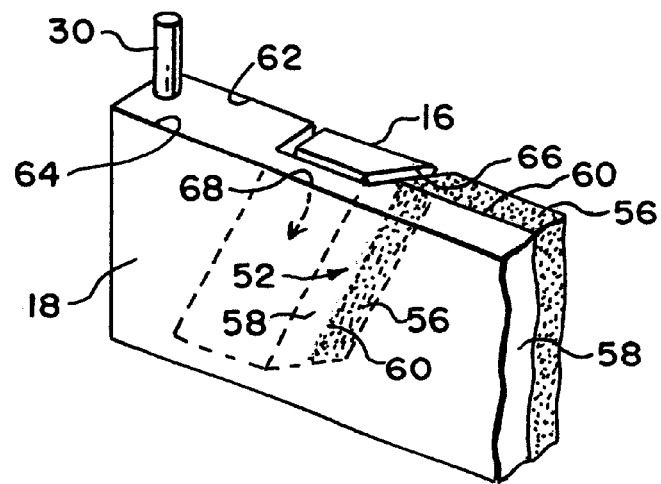
FIG. 5 is an enlarged perspective view of an interface ramp carried by the centrifuge in association with the blood processing chamber, showing the centrifugally separated red blood cell layer, plasma layer, and interface within the chamber when in a desired location on the ramp.

The WB inlet passage 50 channels WB directly into the circumferential flow path immediately next to the PRP collection region 52. As shown in FIG. 5, the WB separates into an optically dense layer 56 of RBC, which forms as RBC move under the influence of centrifugal force toward the high-G wall 62. The movement of RBC 56 displaces PRP radially toward the low-G wall 64, forming a second, less optically dense layer 58.

Centrifugation of WB also forms an intermediate layer 60, also called the interface, which constitutes the transition between the formed cellular blood components and the liquid plasma component. RBC typically occupy this transition region. White blood cells may also occupy this transition region.

Platelets, too, can leave the PRP layer 58 and settle on the interface 60. This settling action occurs when the radial velocity of the plasma near the interface 60 is not enough to keep the platelets suspended in the PRP layer 58. Lacking sufficient radial flow of plasma, the platelets fall back and settle on the interface 60. Larger platelets (greater than about 30 femtoliters) are particularly subject to settling on the interface 60. However, the closeness of the WB inlet region 50 to the PRP collection region 52 in the chamber 22 shown in FIG. 4 creates strong radial flow of plasma into the PRP collection region 52. The strong radial flow of plasma lifts platelets, large and small, from the interface 60 and into the PRP collection region 52.

Further details of the separation chamber 22 are not material to the invention and can be found in U.S. Pat. No. 5,316,667, previously mentioned.

C. The Interface Controller

As FIG. 5 shows, a ramp 66 extends from the high-G wall 62 of the bowl 16 at an angle across the PRP collection region 52. The angle, measured with respect to the axis of the PRP collection port 30 is preferably about 30°. FIG. 5 shows the orientation of the ramp 66 when viewed from the low-G wall 64 of the spool 18. FIG. 4 shows, in phantom lines, the orientation of the ramp 66 when viewed from the high-G wall 62 of the bowl 16.

Further details of the angled relationship of the ramp 66 and the PRP collection port 30 are not material to the invention. They can be found in U.S. patent application Ser. No. 08/472,561, filed Jun. 7, 1995, now U.S. Pat. No. 5,632,893, and entitled "Enhanced Yield Blood Processing System with Angled Interface Control Surface," which is incorporated herein by reference.

The ramp 66 forms a tapered wedge that restricts the flow of fluid toward the PRP collection port 30. The top edge of the ramp 66 extends to form a constricted passage 68 along the low-G wall 64. PRP must flow through the constricted passage 68 to reach the PRP collection port 30.

As FIG. 5 shows, the ramp 66 diverts the fluid flow along the high-G wall 62. This flow diversion changes the orientation of the interface 60 between the RBC layer 56 and the PRP layer 58 within the PRP collection region 52. The ramp 66 thereby displays the RBC layer 56, PRP layer 58, and interface 60 for viewing through the low-G wall 64 of the chamber 22.

The interface controller 12 includes a viewing head 70 (see FIGS. 1 and 8) carried on the yoke 20. The viewing head 70 is oriented to optically view the transition in optical density between the RBC layer 56 and the PRP layer 58 on the ramp 66. The interface controller 12 analyzes the optical data obtained by the viewing head 70 to derive the location of the interface 60 on the ramp 66 relative to the constricted passage 68.

Figure 6:
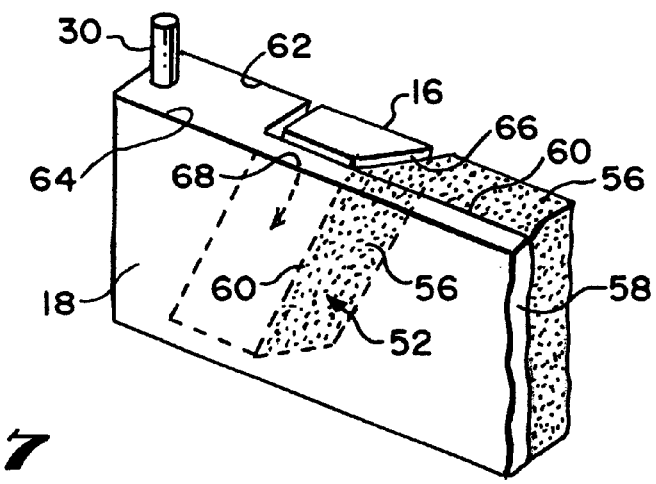
FIG. 6 is an enlarged perspective view of the interface ramp shown in FIG. 5, showing the red blood cell layer and interface at an undesired high location on the ramp.
Figure 7:
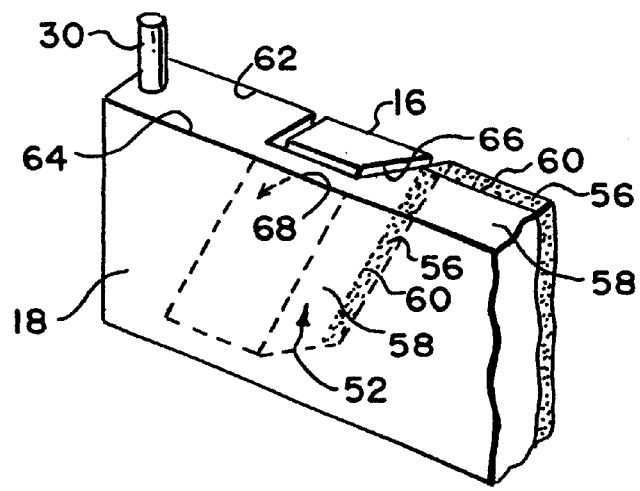
FIG. 7 is an enlarged perspective view of the interface ramp shown in FIG. 5, showing the red blood cell layer and interface at an undesired low location on the ramp.

The location of the interface 60 on the ramp 66 can dynamically shift during blood processing, as FIGS. 6 and 7 show. The interface controller 12 varies the rate at which PRP is drawn from the chamber 22 to keep the interface 60 at a prescribed location on the ramp 66 (which FIG. 5 shows).

Maintaining the interface 60 at a prescribed location on the ramp 66 is important. If the location of the interface 60 is too high (that is, if it is too close to the constricted passage 68 leading to the PRP collection port 30, as FIG. 6 shows), RBC, and, if present, white blood cells can spill over and into the constricted passage 68, adversely affecting the quality of PRP. On the other hand, if the location of the interface 60 is too low (that is, if it resides too far away from the constricted passage 68, as FIG. 7 shows), the fluid dynamics advantageous to effective platelet separation can be disrupted. Furthermore, as the distance between the interface 60 and the constricted passage 68 increases, the difficulty of drawing larger platelets into the PRP flow increases. As a result, a distant interface location results in collection of only the smallest platelets, and overall platelet yield will, as a consequence, be poor.

(1) The Interface Viewing Head

Figure 8:
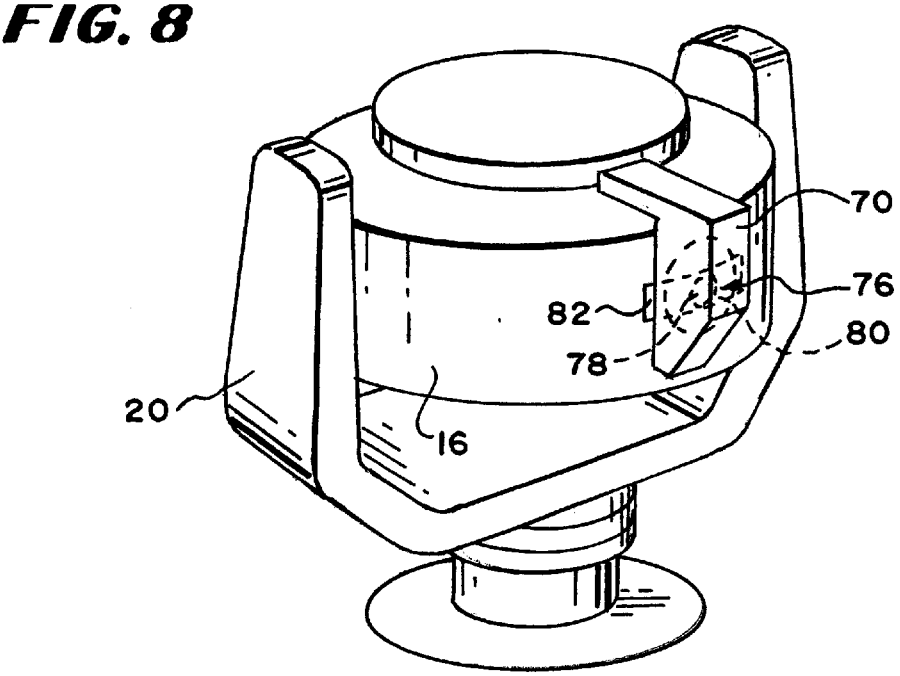
FIG. 8 is a side perspective view of the bowl and spool of the centrifuge when in the operating position, showing the viewing head, which forms a part of the interface controller, being carried by the centrifuge to view the interface ramp during rotation of the bowl.
Figure 9:
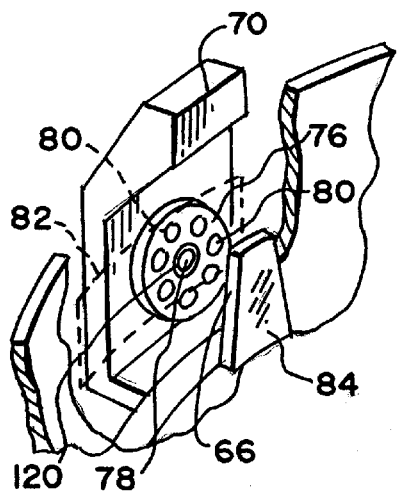
FIG. 9 is a perspective view of the viewing head, with portions broken away and in section, showing the light source and light detector, which are carried by the viewing head, in alignment with the interface ramp, as viewed from within the spool and bowl of the centrifuge.
Figure 10:
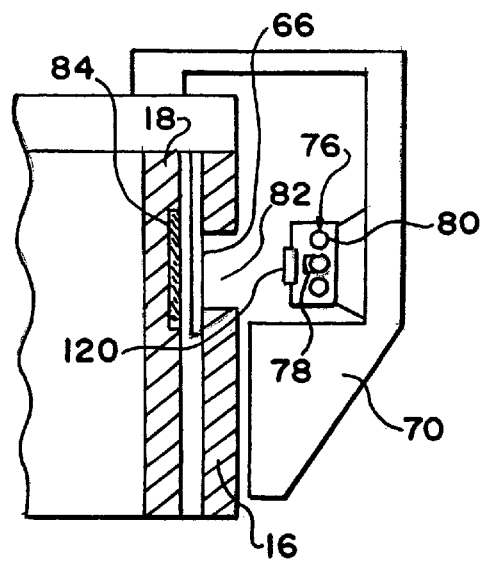
FIG. 10 is a side section view of the bowl, spool, and viewing head when the viewing head is aligned with the interface ramp.

Referring to FIGS. 8 to 10, the viewing head 70, carried by the yoke 20, includes a light source 76, which emits light that is absorbed by RBC. In the illustrated and preferred embodiment, the light source 76 includes a circular array of red light emitting diodes 80. Of course, other wavelengths absorbed by RBC, like green or infrared, could be used.

In the illustrated embodiment, seven light emitting diodes 80 comprise the light source 76. More diodes 80 may be used, or fewer diodes 80 can be used, depending upon the optical characteristics desired.

The viewing head 70 also includes a light detector 78 (see FIGS. 9 and 10), which is mounted adjacent to the light source 76. In the illustrated and preferred embodiment, the light detector 78 comprises a PIN diode detector, which is located generally in the geometric center of the circular array of light emitting diodes 80.

The yoke 20 and viewing head 70 rotate at a one omega speed, as the spool 18 and bowl 16 rotate at a two omega speed. The light source 76 directs light onto the rotating bowl 16. In the illustrated embodiment (see FIG. 8), the bowl 16 is transparent to the light emitted by the source 76 only in the region 82 where the bowl 16 overlies the interface ramp 66. In the illustrated embodiment, the region 82 comprises a window cut out in the bowl 16. The remainder of the bowl 16 that lies in the path of the viewing head 70 comprises a light absorbing material.

The interface ramp 66 is made of a light transmissive material. The light from the source 76 will thereby pass through the transparent region 82 of the bowl 16 and the ramp 66 every time the rotating bowl 16 and viewing head 70 align. The spool 18 may also carry a light reflective material 84 behind the interface ramp 66 to enhance its reflective properties. The spool 18 reflects incoming light received from the source 76 out through the transparent region 82 of the bowl 16, where it is sensed by the detector 78. In the illustrated embodiment, light passing outward from the source 76 and inward toward the detector 78 passes through a focusing lens 120 (shown in FIGS. 9 and 10), which forms a part of the viewing head 70.

The arrangement just described optically differentiates the reflective properties of the interface ramp 66 from the remainder of the bowl 16. This objective can be achieved in other ways. For example, the light source 76 could be gated on and off with the arrival and passage of the ramp 66 relative to its line of sight. As another example, the bowl 16 outside the transparent region 82 could carry a material that reflects light, but at a different intensity than the reflective material 84 behind the interface ramp 66.

As the transparent interface region 82 of the bowl 16 comes into alignment with the viewing head 70, the detector 78 will first sense light reflected through the plasma layer 58 on the ramp 66. Eventually, the RBC layer 56 adjacent the interface 60 on the ramp 66 will enter the optical path of the viewing head 70. The RBC layer 56 absorbs light from the source 76 and thereby reduces the previously sensed intensity of the reflected light. The intensity of the reflected light sensed by the detector 78 represents the amount of light from the source 76 that is not absorbed by the RBC layer 56 adjacent to the interface 60.

(2) The Interface Control System

Figure 11:
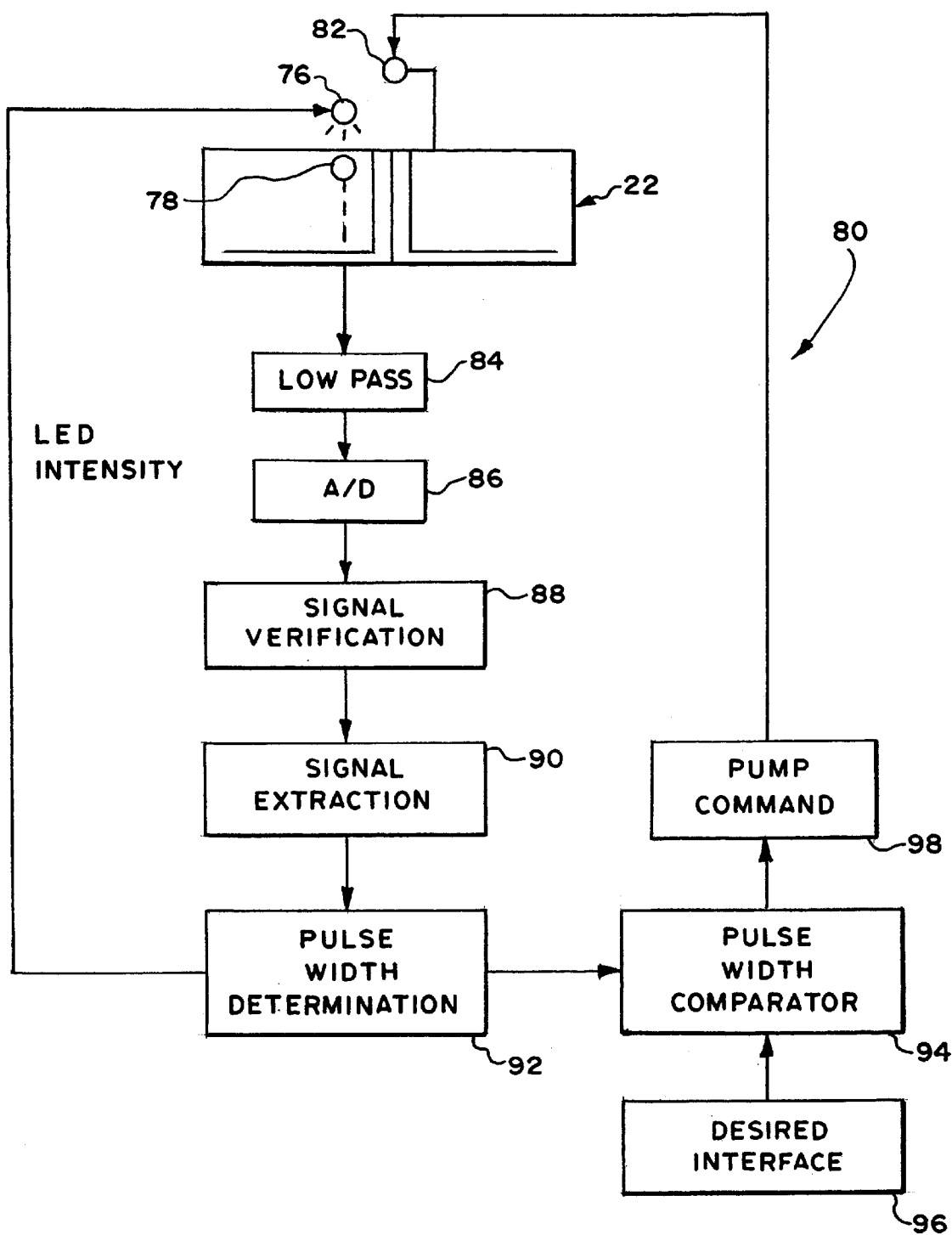
FIG. 11 is a block diagram of an interface control system that embodies various features of the invention and operates to maintain the interface at the desired location on the ramp.

An interface control system 80 incorporated into the interface controller 12 is shown in block diagram form in FIG. 11. As shown, a pump 82 is provided for drawing PRP from the separation chamber 22. In general, the location of the interface 60 relative to the ramp 66 can be controlled by controlling the rate at which PRP is withdrawn from the separation chamber 22. This, in turn, can be controlled by controlling the operating rate of the pump 82. In general terms, the interface control system functions to monitor the position of the interface 60 on the ramp 66 and to adjust the operating speed of the pump 80 so as to keep the interface 60 within a desired zone on the ramp 66.

As further illustrated in FIG. 11, the output of the light detector 78 is coupled through a low pass filter 84 to an analog to digital converter 86. As the ramp 66 rotates past the light source 76 and detector 78, the resulting signal sensed by the sensor 78 is converted to digital form for further processing by the system 80. In the illustrated embodiment, the output signal from the detector 78 is sampled every 15 $\mu$s. It will be appreciated that other sampling rates can be used.

For a number of reasons, it is possible that the light detector 78 might provide a signal output or artifact that is not truly indicative of the actual presence of the ramp adjacent the light source 76 and detector 78 or of the actual location of the interface 60 on the ramp 66. To avoid system response to such false signals or artifacts, the interface control system 80 includes a signal verification subsystem 88 coupled to the output of the analog to digital converter 86. Generally, and in accordance with one aspect of the invention, the signal verification subsystem 88 functions to assess the output pulses provided by the detector 78 and verify that the pulses are, in fact, valid and truly representative of actual operating conditions within the centrifuge. Details of the construction and operation of the signal verification subsystem 88 are provided below with reference to FIG. 12.

Once the existence of valid output signals from the detector 78 is verified, the system 80 next extracts one or more of the signals for further use and analysis. To this end, the interface control system 80 further includes a signal extraction subsystem 90 coupled to the output of the signal verification subsystem 88. In the illustrated embodiment, the signal extraction subsystem 90 functions to time average and align five verified, individually acquired signals from the detector 78 and produce a single composite signal based on the time average of the individual signals. The composite signal thus produced is what is then passed along for further analysis and use by the system 80. Details of the construction and operation of the signal extraction subsystem 88 are provided below with reference to FIG. 13.

Analysis of the composite signal provided by the signal extraction subsystem 90 is accomplished in a pulse width determination subsystem 92 constructed in accordance with various aspects of the invention. The pulse width determination subsystem 92 functions broadly to determine the width of the pulses detected by the detector 78 and to develop a signal indicative of the detected pulse width. The detected pulse width is then fed to a pulse width comparator 94 that compares the detected pulse width against a known, desired interface standard 96. Depending upon whether the detected pulse width is greater than, less than, or within desired operating limits, the pulse width comparator 94 signals a pump command circuit 98 to increase, decrease or maintain the speed of the pump 82 to keep the interface 60 within desired limits on the ramp 66.

In accordance with one aspect of the invention, the pulse width determination subsystem 92 determines the pulse width of the detected pulses through a sophisticated analysis of several signal parameters beyond simply signal passage above and below preestablished threshold limits. As will be developed more fully below with respect to FIG. 14, the pulse width determination subsystem 92 takes into account such signal features as signal shape, slope, inflection points, etc., in determining the width of the detected pulses. Such sophisticated analysis of the detected pulses results in more accurate determination of the actual interface position on the ramp 66 and more accurate and effective collection of desired blood constituents.

Figure 12:
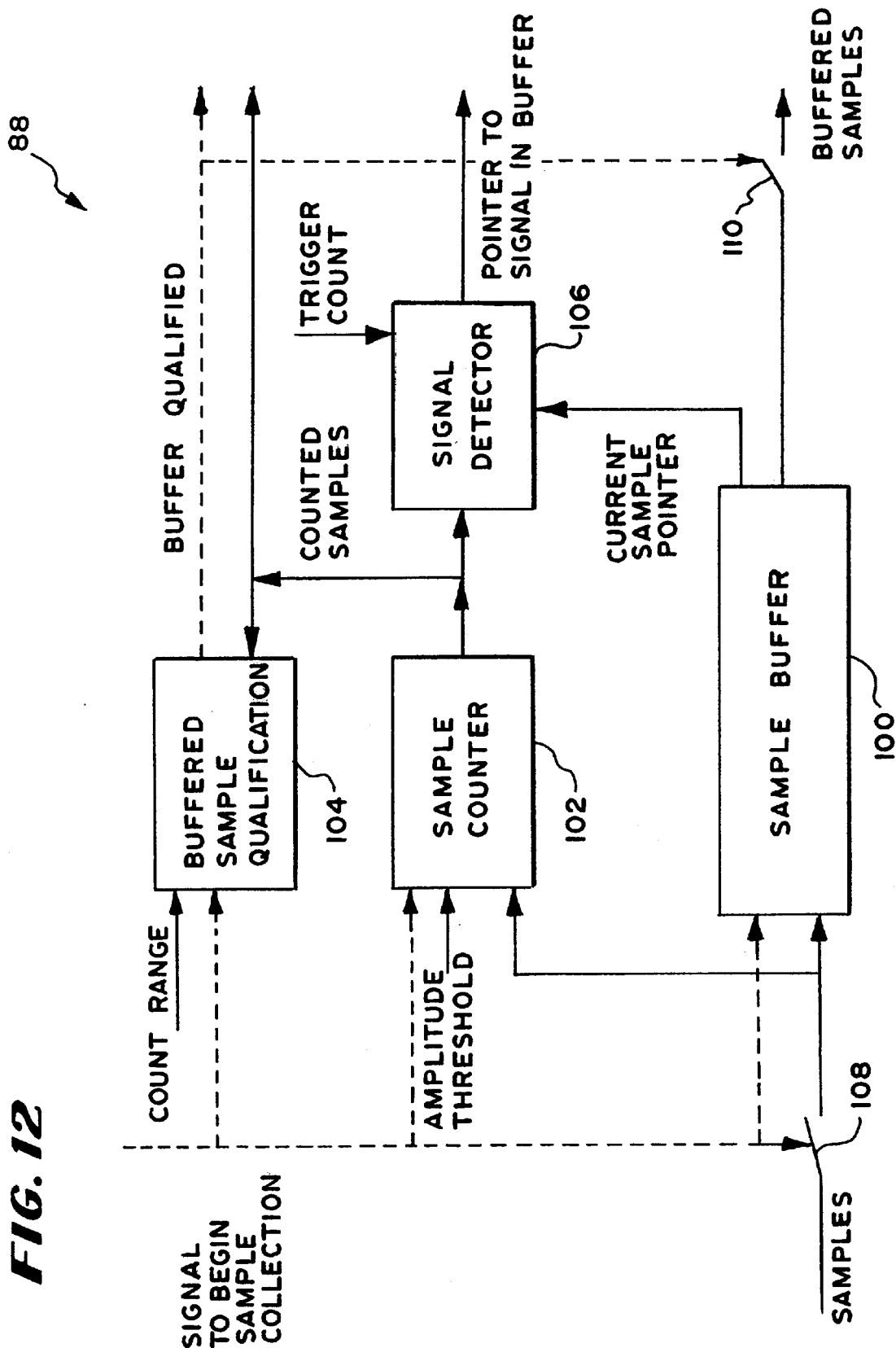
FIG. 12 is a block diagram of the signal verification subsystem included in the control system of FIG. 11.

The signal verification subsystem 88 is shown in greater detail in FIG. 12. As noted, the primary function of the signal verification subsystem is to verify that the signals from the detector 78 are valid and are likely to contain truthful information regarding conditions sensed at the ramp 66. As shown, the signal verification subsystem 88 includes a sample buffer 100, a sample counter 102, a buffered sample qualification circuit 104 and a signal detector circuit 106. A first controllable switch 108 is coupled to the input of the sample buffer 100, while a second controllable switch 110 is coupled to the output of the sample buffer 100.

System operation begins with a signal to begin sample collection. This signal, which is generated elsewhere in the centrifuge 10 and indicates that fluid processing is beginning, has the effect of closing the first switch 108 and enabling the sample counter 102 and buffered sample qualifier 104. When the first switch 108 is closed, signals or samples detected by the detector 78 (FIG. 11) are loaded into the sample buffer 100. The sample buffer 100 generates a "current sample pointer" signal, which indicates the address at which samples entering the buffer 100 will be written. The "current sample pointer" is reset to zero at the start of sampling and is incremented each time a sample is written into the buffer 100.

The samples are also loaded into the sample counter 102. The sample counter 102 functions to compare each sample against a predetermined amplitude threshold to verify that the magnitude of the sample is greater than the threshold. Preferably, the threshold is above the noise floor of the system but below the peak value of the expected signal. This helps ensure that the system 88 is responding to legitimate signals developed by the detector 78 and not to random noise or artifacts.

Samples that exceed the amplitude threshold are applied to the buffered sample qualification subsystem 104. When enabled by the signal to begin sample collection, the buffered sample qualification subsystem 104 further verifies the validity of the samples by performing a time-based check on when the samples occur. In particular, the buffered sample qualification system 104 functions to determine whether the samples occur when the sensor 78 is adjacent the ramp 66 or at some other time. Only those samples that occur when the sensor 78 is adjacent the ramp 66 are considered valid. To this end, a "count range" signal is developed as the centrifuge operates and is applied to the buffered sample qualification subsystem 104. The "count range" signal is derived from the relative positions of the sensor 78 and the ramp 66 and defines the beginning and end of the period during each revolution of the centrifuge during which the sensor 78 and ramp 66 are properly aligned. If the sample occurs during the desired "count range," the buffered sample qualification subsystem 104 generates a "buffer qualified" control signal. The presence of the "buffer qualified" control signal indicates to the remainder of the system that the samples in the sample buffer 100 have been properly qualified by the sample counter 102 and the buffered sample qualification subsystem 104.

Samples that are properly qualified by the sample counter 102 are also applied to the signal detector circuit 106. The signal detector circuit 106 also receives the "current sample pointer" signal generated by the sample buffer 100 as well as a "trigger count" signal that represents the minimum value of "counted samples" necessary to indicate that the "buffered samples" contain the expected signal. The signal detector circuit 106 compares the "counted samples" against the "trigger count" and develops a "pointer to signal in buffer" that indicates the buffer address at which the "counted samples" equals the "trigger count." This provides a rough estimate of the location of the interface signal in the buffered samples.

Figure 13:
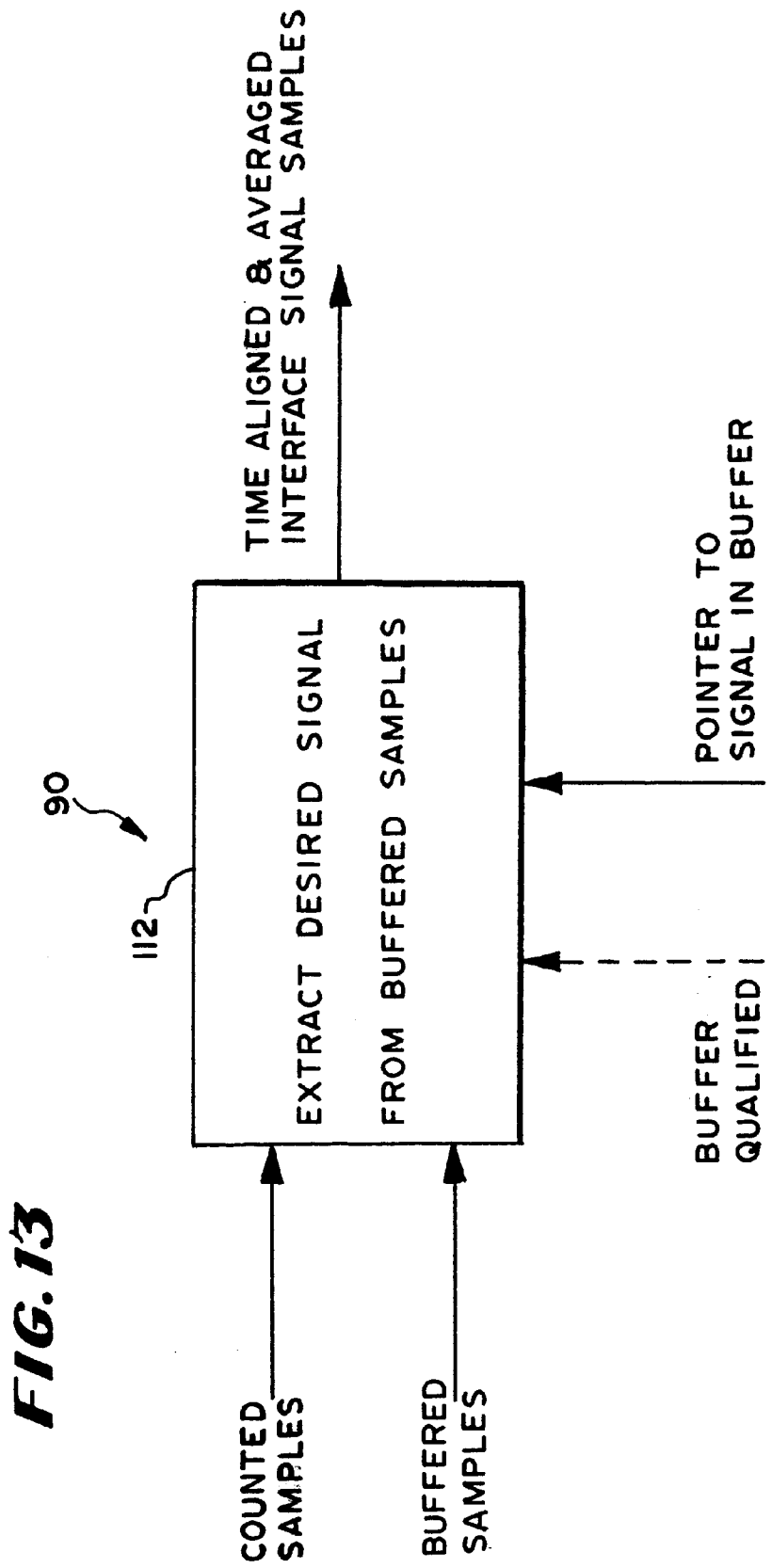
FIG. 13 is a block diagram of the signal extraction subsystem included in the control system of FIG. 11.

The various control and data signals developed and provided by the signal verification subsystem 88 are applied to the signal extraction subsystem 90 shown in FIG. 13. The signal extraction subsystem 90 functions broadly to time align and average a predetermined number of samples acquired and qualified by the signal verification subsystem 88 to recreate the output signals of the detector 78 acquired as the ramp 66 passes by. In the illustrated embodiment, the signal extraction subsystem time aligns and averages qualified samples representing five such passages. It will be appreciated that a greater or lesser number of qualified samples can be selected. The output of the signal extraction subsystem 90 comprises a time-varying waveform representing the output signal provided by the detector 78 as averaged over five passes of the ramp 66 past the detector 78.

Figure 14:
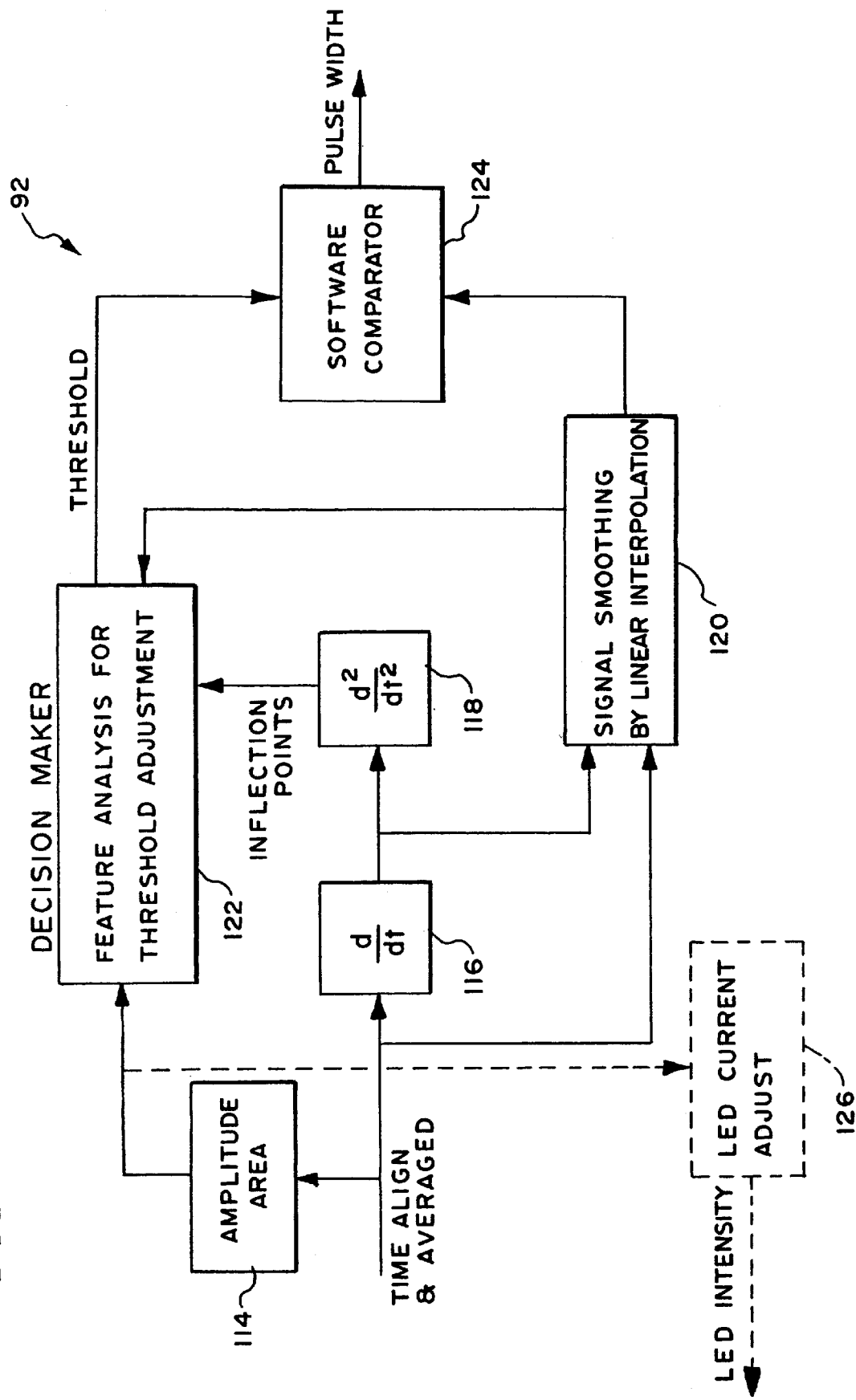
FIG. 14 is block diagram of the pulse width determination subsystem of the control system of FIG. 11.

The time aligned and averaged composite sample signal developed by the signal extraction subsystem 90 is then applied to the pulse width determination subsystem 92 shown in detail in FIG. 14. In accordance with one aspect of the invention, the pulse width determination subsystem 92 functions to analyze such signal parameters as peak amplitude, total pulse area, area enclosed by threshold and slope changes on the leading edge of the signal. These signal parameters can be used to obtain greater knowledge of the actual position of the interface than was provided by prior systems that simply compared signal amplitude against a fixed threshold to sense signal pulse width.

As shown in FIG. 14, the pulse width determination system 92 includes an amplitude/area determining circuit 114 that operates to sense both the amplitude of, and the area under, the applied time aligned and averaged signals. The system 92 further includes first and second differentiator circuits 116, 118 that determine, respectively, the first and second derivatives of the applied time aligned and averaged waveforms. The system also includes a smoothing circuit 120 that receives the time aligned and averaged signal, and the first derivative thereof, as inputs and generates an output signal that is substantially continuous and a good facsimile of the original output signals obtained from the detector 78. The outputs of the amplitude/area circuit 114, the first differentiator circuit 116, the second differentiator circuit 118, and the signal smoothing circuit 120 are applied to a control circuit or decision maker 122 that, based on these various inputs, determines and generates an appropriate threshold. This threshold is applied to a software comparator 124 which then compares the output of the signal smoothing circuit 120 against the threshold to establish a pulse width associated with the time aligned and averaged sample signal. It will be appreciated that by raising or lowering the threshold, the apparent pulse width of the sample can be made to change without any actual change in the sample itself. The pulse width determination system 92 functions to determine where best to set the threshold so that the resulting pulse width is most likely to give a true representation or indication of position of the interface 66 relative to the ramp 60. Unlike in prior systems, the pulse width determination system of the present invention takes into consideration various characteristics of the signal, such as wave shape and slope, is selecting where to set the threshold.

The pulse width determination system 92 further includes an LED current adjust circuit 126 that is coupled to the amplitude/area determining circuit 114 and that controls current in the source LEDs 76. Preferably, the LED current adjust circuit 126 controls the LED current so that the area under the resulting time aligned and averaged signal is between preestablished upper and lower limits.

Because the pulse width determination system 92 is capable of sensing and responding to a variety of signal characteristics and parameters, the system is capable of recognizing and compensating for various known discrepancies in the sensed signals. Several of these conditions are shown in FIGS. 15–18.

Figure 15:
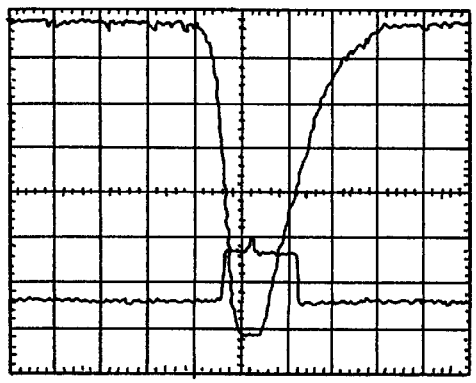
FIG. 15 is a waveform diagram of a signal appearing at the output of the optical detector, depicting what is considered a "normal" interface signal of the type leading to good platelet yield and low WBC count.

FIG. 15 depicts what is considered a "normal" interface signal that leads to good platelet yield and low WBC count. The signal is characterized by smooth trailing and leading edges free from inflection points or humps. With such a waveform, the threshold level can be set at any point between the absolute maximum and minimum values of the waveform, and the pulse width can be defined as the width between the resulting crossing points. Typically, the threshold can be determined at the start of a procedure and will remain fixed until the end of the procedure, provided the shape of the signal does not change, particularly with regard to amplitude and the shape of the leading edge.

Figure 16:
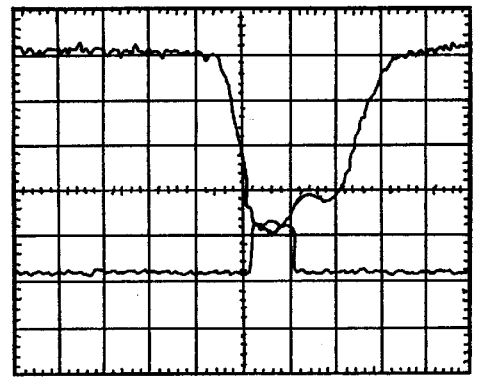
FIG. 16 is a waveform diagram similar to FIG. 15 showing a signal displaying a "camel phenomenon" that is sometimes observed during collection procedures.

FIG. 16 shows a signal displaying a "camel phenomenon" that is sometimes observed during collection procedures. When thresholds are set below the level of the "hump", platelet yield is usually low. If the threshold is set significantly above the hump, this has been found to cause RBC flow over the ramp. Accordingly, the optimum threshold setting when the "camel phenomenon" occurs is just above the level of the hump. By ascertaining the first and second derivatives of the pulse leading edge, the pulse width determination system 92 can determine where the peak of the hump is and can thereafter place the threshold at that level or some predetermined amount above that level. If the waveform changes as the platelet collection procedure continues, the system 92 will automatically readjust the threshold to maintain it at the desired position. Similarly, if the "camel phenomenon" terminates during the procedure and the signal waveform returns to normal, (FIG. 15), the system 92 will automatically reinstate the normal, predetermined threshold.

Figure 17:
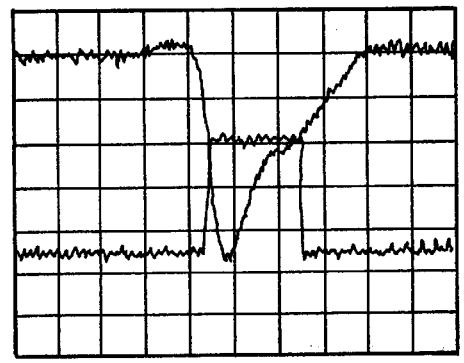
FIG. 17 is a waveform diagram similar to FIG. 15 showing an inflection point that sometimes occurs in the leading edge of the waveform.

Still another frequently encountered abnormal waveshape is shown in FIG. 17. In this waveform, an inflection point occurs in the leading edge of the waveform. Although the exact cause of this phenomenon is not fully understood at this time, it is believed to be possibly caused by an accumulation of platelets on the ramp 66. Signals exhibiting this waveform are also frequently characterized by an oscillating amplitude which decreases with an increase in platelets on the ramp and increases when the cells are washed off. If the threshold is located above the inflection point, a high WBC frequently results. When this phenomenon occurs, the corrective action is to place the threshold below the inflection point. By ascertaining the second derivative of the sample signal, the system 92 can readily determine the inflection point and thereafter set the threshold at, or some predetermined distance below, the inflection point. Again, the system 92 can automatically change the threshold on a substantially continuous basis to adapt to changes in operating conditions and changes in the signal waveform.

Figure 18:
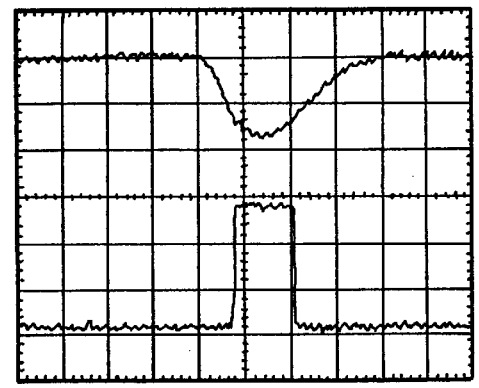
FIG. 18 is a waveform diagram similar to FIG. 15 showing a signal that frequently results when the donor is lipemic or has a high platelet count.

FIG. 18 shows a signal that frequently results when the donor is lipemic or has a high platelet count. With this condition, light transmissitivity through the blood is low and the signal amplitude drops and remains low throughout the procedure. Platelet collection efficiency can be low. To compensate for the low transmissive property of the blood, the system 92 increases the intensity of the source LEDs 76. By increasing the LED current, source brightness is increased and leads to a higher amplitude signal. The signal peak amplitude is used as a feedback parameter for controlling the LED current with the aim, in the illustrated embodiment, of keeping the signal amplitude in the 12–14 V range. Maximum LED current is limited to avoid shortening LED life and, in the illustrated embodiment, is limited to 30 mA. It is possible that even at peak LED brightness, the signal peak amplitude cannot be brought into the desired range. In this case, the system 92 sets the threshold the area enclosed by the threshold is 50% of the total area bounded by the signal. It will be appreciated that other operating parameters can also be used.

The system 92 herein shown and described offers operating flexibility beyond that provided by prior systems. In particular, the ability to sense and analyze such signal features as shape and area enables the system 92 to recognize abnormal operating conditions and compensate for them on a dynamic real time basis as a collection procedure proceeds. Although various operating examples have been described for illustrative purposes, it will be appreciated that the system 92 can easily be programmed to operate in other modes and that these examples are meant to be illustrative rather than limiting.

While a particular embodiment of the invention has been shown and described, it will be obvious to those skilled in the art that changes and modifications can be made without departing from the invention in its broader aspects, and, therefore, the aim in the appended claims is to cover all such changes and modifications as fall within the true spirit and scope of the invention.

We claim:

1. A centrifugal blood processing system comprising:
   a centrifuge assembly having a rotatable element for subjecting blood to centrifugation into a first blood component, a second blood component, and an interface region between the two blood components, the rotatable element including a surface along which the interface region is displayed during centrifugation;

an optical assembly external to the rotatable element operating to view the surface within the rotatable element during centrifugation and to develop a signal indicative of the position of the interface region relative to the surface, the signal having a discernable wave shape;

a signal processor operating to discern an inflection point on the wave shape and to develop a control output; and control circuitry coupled to the centrifuge assembly and operating in response to the control output to control the operation of the centrifuge assembly to maintain the position of the interface region within a desired zone relative to the surface.

2. A centrifugal blood processing system as defined in claim 1 wherein the signal includes a discernable area; and wherein the signal processor includes an integrator to discern the area of the signal.

3. A centrifugal blood processing system as defined in claim 1 wherein the signal processor includes a differentiator to discern the wave shape of the signal.

4. A centrifugal blood processing system as defined in claim 3 wherein the signal processor further includes a second differentiator to discern presence or absence of an inflection point in the signal.

5. A centrifugal blood processing system as defined in claim 1 wherein the signal has a peak amplitude, and wherein the signal processor further includes an element operating to discern the peak amplitude of the signal.

6. A centrifugal blood processing system as defined in claim 1 wherein the signal includes a discernable area;

wherein the optical assembly further includes a light source having a variable intensity;

wherein the signal processor includes an element operating to discern the area of the signal and generate an additional control output based upon the discerned area; and wherein the control circuitry operates in response to the additional control output to control the intensity of the light source.

7. A centrifugal blood processing system as defined in claim 6 wherein the control circuitry operates to control the intensity of the light source to maintain the discerned area of the signal within preestablished limits.

8. A centrifugal blood processing system as defined in claim 1 wherein the control circuitry operates to classify the signal into one of a plurality of predefined categories.

9. A centrifugal blood processing system as defined in claim 8 wherein the categories are based at least in part on the wave shape of the signal.

10. An interface position control system for controlling the position of an interface between the component layers of blood during centrifugation within a rotating field, comprising:

an energy source external to the rotating field operable to direct energy onto the interface within the rotating field, the energy thus directed being substantially absorbed by one of the component layers and substantially reflected by the other of the component layers;

a sensor assembly external to the rotating field operating to sense the energy reflected by the reflective one of the component layers and to develop a signal indicative of the intensity of the reflected energy, the signal having a discernable signal characteristic;

a signal processor operating to discern the signal characteristic and generate an output that classifies the signal into one of a plurality of predefined categories; and a control system coupled to the signal processor and operating to control the operating parameters of the blood centrifugation process in accordance with the output of the signal processor.

11. An interface position control system as defined in claim 10 wherein the discernable signal characteristic is a wave shape;

wherein the signal processor includes a differentiator to discern the wave shape and a comparator to compare the wave shape to a plurality of predetermined wave shape categories and classify the wave shape into one of the categories.

12. A method of processing blood within a rotating field using a centrifuge of the type having a constituent interface viewing surface carried within the rotating field and an optical detector external to the rotating field for developing a signal indicative of the position of a constituent interface relative to the constituent interface viewing surface, the method comprising the steps of:

discerning the wave shape of the signal;

comparing the discerned wave shape against a plurality of predetermined wave shape categories to classify the discerned wave shape as one of the categories; and varying operating parameters of the centrifuge in accordance with the classification of the discerned wave shape.

13. A centrifugal blood processing system comprising:

a centrifuge assembly having a rotatable element for subjecting blood to centrifugation into a first blood component, a second blood component, and an interface region between the two blood components, the rotatable element including a surface along which the interface region is displayed during centrifugation;

an optical assembly external to the rotatable element operating to view the surface within the rotatable element during centrifugation and to develop a signal indicative of the position of the interface region relative to the surface, the signal having a discernable wave shape and a discernable amplitude;

a signal processor operating to discern the wave shape and the amplitude of the signal and to develop a control output based on the discerned wave shape and discerned amplitude of the signal, the signal processor including a first differentiator for discerning the wave shape and a second differentiator for discerning inflection points in the wave shape; and control circuitry coupled to the centrifuge assembly and operating in response to the control output to control the operation of the centrifuge assembly to maintain the position of the interface region within a desired zone relative to the surface.

14. A centrifugal blood processing system as defined in claim 13
   wherein the signal includes a discernable area; and
   wherein the signal processor includes an integrator operating to discern the area of the signal.

15. A centrifugal blood processing system as defined in claim 13
   wherein the signal processor includes an element operating to sense peak amplitude of the signal.

16. A centrifugal blood processing system as defined in claim 13
   wherein the signal includes a discernable area;
   wherein the optical assembly includes a light source having a variable intensity;
   wherein the signal processor includes an element operating to discern the area of the signal and generate an additional control output based upon the discerned area; and
   wherein the control circuitry operates in response to the additional control output to control the intensity of the light source.

17. A centrifugal blood processing system as defined in claim 16
   wherein the control circuitry operates to control the intensity of the light source to maintain the discerned area of the signal within preestablished limits.

18. A centrifugal blood processing system as defined in claim 13
   wherein the control circuitry operates to classify the signal into one of a plurality of predefined categories.

19. A centrifugal blood processing system as defined in claim 18
   wherein the categories are based, at least in part, on the discerned wave shape of the signal.

20. A centrifugal blood processing system comprising:
   a centrifuge assembly having a rotatable element for subjecting blood to centrifugation into a first blood component, a second blood component, and an interface region between the two components, the rotatable element including a surface along which the interface region is displayed during centrifugation;
   an optical assembly external to the rotatable element operating to view the surface within the rotatable element during centrifugation and to develop a signal indicative of the position of the interface region relative to the surface, the signal having a discernable wave shape and a discernable amplitude;
   a signal processor operating to discern the wave shape and the amplitude of the signal and to classify the signal into one of a plurality of predefined categories, the signal processor operating further to develop a control output based on the classification of the signal; and
   control circuitry coupled to the centrifuge assembly and operating in response to the control output to control the operation of the centrifuge assembly to maintain the position of the interface region within a desired zone relative to the surface.

21. A centrifugal blood processing system comprising:
   a centrifuge assembly having a rotatable element for subjecting blood to centrifugation into a first blood component, a second blood component, and an interface region between the two components, the rotatable element including a surface along which the interface region is displayed during centrifugation;
   an optical assembly external to the rotatable element operating to view the surface within the rotatable element during centrifugation and to develop a signal indicative of the position of the interface region relative to the surface, the signal having a discernable wave shape and a discernable amplitude;
   a signal processor operating to discern the wave shape and the amplitude of the signal and to classify the signal into one of a plurality of predefined categories based, at least in part, on the discerned wave shape of the signal, the signal processor operating further to develop a control output based on the classification of the signal; and
   control circuitry coupled to the centrifuge assembly and operating in response to the control output to control the operation of the centrifuge assembly to maintain the position of the interface region within a desired zone relative to the surface.

22. A centrifugal blood processing system as defined in claim 20 or 21
   wherein the signal includes a discernable area; and
   wherein the signal processor includes an integrator operating to discern the area of the signal.

23. A centrifugal blood processing system as defined in claim 20 or 21
   wherein the signal processor includes an element operating to sense peak amplitude of the signal.

24. A centrifugal blood processing system as defined in claim 20 or 21
   wherein the signal includes a discernable area;
   wherein the optical assembly includes a light source having a variable intensity;
   wherein the signal processor includes an element operating to discern the area of the signal and generate an additional control output based upon the discerned area; and
   wherein the control circuitry operates in response to the additional control output to control the intensity of the light source.

25. A centrifugal blood processing system as defined in claim 24
   wherein the control circuitry operates to control the intensity of the light source to maintain the discerned area of the signal within preestablished limits.

26. An interface position control system for controlling the position of an interface between the component layers of blood during centrifugation within a rotating field, comprising:
   an energy source external to the rotating field operating to direct energy onto the interface within the rotating field, the energy thus directed being substantially absorbed by one of the component layers and substantially reflected by the other of the component layers;
   a sensor assembly external to the rotating field operating to sense the energy reflected by the reflective one of the component layers and to develop a signal indicative of the intensity of the reflected energy, the signal having a discernable amplitude, duration, and wave shape that vary according to the intensity of the reflected energy;
   a signal processor operating to discern the amplitude, duration and wave shape of the signal and generate an output based upon the discerned amplitude, duration, and wave shape of the signal, the signal processor including an element to discern the peak amplitude of the signal;

a comparator coupled to the signal processor and operating to compare the wave shape of the signal to preselected known wave shapes and generate an output based upon the comparison; and a control system coupled to the signal processor and to the comparator and operating to control the operating parameters of the centrifugation process in accordance with the outputs of the signal processor and comparator.

27. An interface position control system for controlling the position of an interface between the component layers of blood during centrifugation within a rotating field, comprising:

an energy source external to the rotating field operating to direct energy onto the interface within the rotating field, the energy thus directed being substantially absorbed by one of the component layers and substantially reflected by the other of the component layers;

a sensor assembly external to the rotating field operating to sense the energy reflected by the reflective one of the component layers and to develop a signal indicative of the intensity of the reflected energy, the signal having a discernable amplitude, duration, and wave shape that vary according to the intensity of the reflected energy;

a signal processor operating to discern the amplitude, duration and wave shape of the signal and generate an output based upon the discerned amplitude, duration, and wave shape of the signal;

a comparator coupled to the signal processor and operating to compare the wave shape of the signal to preselected known wave shapes and generate an output based upon the comparison; and a control system coupled to the signal processor and to the comparator and operating based upon the outputs of the signal processor and comparator to classify the signal into one of a plurality of predefined categories and to control the operating parameters of the centrifugation process based, at least in part, upon the classification of the signal.

28. An interface position control system for controlling the position of an interface between the component layers of blood during centrifugation within a rotating field, comprising:

an energy source external to the rotating field operating to direct energy onto the interface within the rotating field, the energy thus directed being substantially absorbed by one of the component layers and substantially reflected by the other of the component layers;

a sensor assembly external to the rotating field operating to sense the energy reflected by the reflective one of the component layers and to develop a signal indicative of the intensity of the reflected energy, the signal having a discernable amplitude, duration, and wave shape that vary according to the intensity of the reflected energy;

a signal processor operating to discern the amplitude, duration and wave shape of the signal and generate an output based upon the discerned amplitude, duration, and wave shape of the signal;

a comparator coupled to the signal processor and operating to compare the wave shape of the signal to preselected known wave shapes and generate an output that classifies the wave shape into one of a plurality of predefined categories; and a control system coupled to the signal processor and to the comparator and operating to control the operating parameters of the centrifugation process in accordance with the outputs of the signal processor and comparator.

29. An interface position control system as defined in claim 26 or 27 or 28 wherein the signal includes a discernable area; and wherein the signal processor includes an integrator operating to discern the area of the signal.

30. An interface position control system as defined in claim 26 or 27 or 28 wherein the signal processor includes a differentiator for discerning the wave shape.

31. An interface position control system as defined in claim 27 wherein the signal processor includes a second differentiator for discerning inflection points in the wave shape.

32. An interface position control system as defined in claim 26 or 27 or 28 wherein the signal includes a discernable area;

wherein the sensor assembly includes a light source having a variable intensity;

wherein the signal processor includes an element operating to discern the area of the signal and generate an additional control output based upon the discerned area; and wherein the control system operates in response to the additional control output to control the intensity of the light source.

33. An interface position control system as defined in claim 32 wherein the control system operates to control the intensity of the light source to maintain the discerned area of the signal within preestablished limits.

34. A method of processing blood within a rotating field using a centrifuge of the type having a constituent interface viewing surface carried within the rotating field and an optical detector external to the rotating field for developing a signal indicative of the position of a constituent interface relative to the constituent interface viewing surface, the method comprising the steps of:

sensing a sensed parameter including the presence or absence of an inflection point in the signal;

comparing the sensed parameter against predetermined standards; and varying operating parameters of the centrifuge in accordance with the sensed predetermined parameters of the signal.

35. A method as defined in claim 34 wherein a parameter of the signal sensed during the sensing step includes the area of the signal.

36. A method as defined in claim 34 wherein a predetermined parameter of the signal sensed during the sensing step includes the peak amplitude of the signal.

37. A method as defined in claim 34 wherein a parameter of the signal sensed during the sensing step includes the shape of the signal.

38. A method as defined in claim 34 comprising the further steps of:

defining a plurality of categories based on possible characteristics of the signal;

classifying the signal into one of the defined categories based on a sensed parameter of the signal; and varying the operating parameters of the centrifuge in accordance with a predetermined protocol selected in accordance with the defined category to which the signal has been classified.

39. A centrifugal blood processing system comprising:

a centrifuge assembly having a rotatable element for subjecting blood to centrifugation into a first blood component, a second blood component, and an interface region between the two blood components, the rotatable element including a surface along which the interface region is displayed during centrifugation;

an optical assembly external to the rotatable element operating to view the surface within the rotatable element during centrifugation and to develop a signal indicative of the position of the interface region relative to the surface, the signal having a discernable signal characteristic;

a signal processor operating to discern the signal characteristic and to classify the signal into one of a plurality of predefined categories, the signal processor operating further to develop a control output based on the classification of the signal; and control circuitry coupled to the centrifuge assembly and operating in response to the control output to control the operation of the centrifuge assembly to maintain the position of the interface region within a desired zone relative to the surface.

40. A centrifugal blood processing assembly as defined in claim 39 wherein the discernable signal characteristic includes a wave shape; and wherein the signal processor includes an element that operates to discern the wave shape and to classify the signal into one of a plurality of predefined categories based, at least in part, upon the discerned wave shape.

41. A centrifugal blood processing system as defined in claim 39 wherein the signal processor further includes an element to discern presence or absence of an inflection point in the wave form.

42. A centrifugal blood processing system as defined in claim 39 wherein the discernable signal characteristic includes a peak amplitude, and wherein the signal processor includes an element operating to discern the peak amplitude of the signal and to classify the signal into one of a plurality of predefined categories based, at least in part, upon the discerned peak amplitude.

43. A centrifugal blood processing system as defined in claim 39 wherein the signal includes a discernable area;

wherein the optical assembly further includes a light source having a variable intensity;

wherein the signal processor includes an element operating to discern the area of the signal and generate an additional control output based upon the discerned area; and wherein the control circuitry operates in response to the additional control output to control the intensity of the light source.

44. A centrifugal blood processing system as defined in claim 43 wherein the control circuitry operates to control the intensity of the light source to maintain the discerned area of the signal within preestablished limits.

45. A centrifugal blood processing system comprising:

a centrifuge assembly having a rotatable element for subjecting blood to centrifugation into a first blood component, a second blood component, and an interface region between the two blood components, the rotatable element including a surface along which the interface region is displayed during centrifugation;

an optical assembly external to the rotatable element operating to view the surface within the rotatable element during centrifugation and to develop a signal having a shape indicative of the position of the interface region relative to the surface, the signal shape having a discernable area, optical assembly including a light source having a variable intensity;

a signal processor operating to discern the area of the signal shape and to develop a control output based on the discerned area; and control circuitry coupled to the centrifuge assembly and operating in response to the control output to control the intensity of the light source.

46. A centrifugal blood processing system as defined in claim 45 wherein the control circuitry operates to control the intensity of the light source to maintain the discerned area of the signal shape within preestablished limits.

47. An interface position control system for controlling the position of an interface between the component layers of blood during centrifugation within a rotating field, comprising:

an energy source external to the rotating field operable to direct energy onto the interface within the rotating field, the energy thus directed being substantially absorbed by one of the component layers and substantially reflected by the other of the component layers;

a sensor assembly external to the rotating field operating to sense the energy reflected by the reflective one of the component layers and to develop a signal indicative of the intensity of the reflected energy, the signal having a discernable wave shape;

a signal processor operating to discern an inflection point on the wave shape and to develop an output based on the presence or absence of an inflection point on the wave shape; and a control system coupled to the signal processor and operating to control the operating parameters of the centrifugation process in accordance with the output of the signal processor.

48. An interface position control system for controlling the position of an interface between the component layers of blood during centrifugation within a rotating field, comprising:

an energy source external to the rotating field operable to direct energy onto the interface within the rotating field, the energy thus directed being substantially absorbed by one of the component layers and substantially reflected by the other of the component layers;

a sensor assembly external to the rotating field operating to sense the energy reflected by the reflective one of the component layers and to develop a signal indicative of the intensity of the reflected energy, the signal including a wave shape having discernable area, the sensor assembly including a light source having a variable intensity;

a signal processor operating to discern the area of the wave shape and to develop an output based on the discerned area; and a control system coupled to the signal processor and operating in response to the output to control the intensity of the light source.

49. An interface position control system as defined in claim 48 wherein the control system operates to control the intensity of the light source to maintain the discerned area of the wave shape within preestablished limits.

* * * * *